(12) United States Patent
Hamashima et al.

(10) Patent No.: US 6,479,819 B1
(45) Date of Patent: Nov. 12, 2002

(54) OBJECT OBSERVATION APPARATUS AND OBJECT OBSERVATION

(75) Inventors: Muneki Hamashima, Urayasu (JP); Yoichi Watanabe, Kawasaki (JP); Yoshiaki Kohama, Kawasaki (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/505,280

(22) Filed: Feb. 16, 2000

Related U.S. Application Data

(63) Continuation-in-part of application No. PCT/JP98/03667, filed on Aug. 19, 1998.

(30) Foreign Application Priority Data

Aug. 19, 1997 (JP) .............................................. 9-222187
Aug. 29, 1997 (JP) .............................................. 9-234466

(51) Int. Cl.[7] .............................................. H01J 37/28
(52) U.S. Cl. ...................................... 250/310; 250/397
(58) Field of Search ................................ 250/310, 397

(56) References Cited

U.S. PATENT DOCUMENTS

| | | | | |
|---|---|---|---|---|
| 3,714,425 | A | | 1/1973 | Someya et al. ............. 250/310 |
| 4,399,360 | A | * | 8/1983 | Fotino ......................... 250/397 |
| 5,498,874 | A | | 3/1996 | Miyoshi et al. ............. 250/397 |
| 5,576,833 | A | | 11/1996 | Miyoshi et al. ............. 250/310 |
| 6,087,659 | A | * | 7/2000 | Adler et al. ................. 250/310 |
| 6,184,526 | B1 | * | 2/2001 | Kohama et al. ............ 250/310 |

FOREIGN PATENT DOCUMENTS

| | | |
|---|---|---|
| JP | 48-31685 | 10/1973 |
| JP | 56-16068 | 2/1981 |
| JP | A-4-242060 | 8/1992 |
| JP | A-7-181297 | 7/1995 |
| JP | A-7-249393 | 9/1995 |
| JP | A-9-270242 | 10/1997 |
| JP | A-10-197462 | 7/1998 |
| JP | A-10-197463 | 7/1998 |

* cited by examiner

Primary Examiner—Jack Berman
(74) Attorney, Agent, or Firm—Oliff & Berridge, PLC

(57) ABSTRACT

This invention relates to an object observation apparatus and observation method. The object observation apparatus is characterized by including a drivable stage on which a sample is placed, an irradiation optical system which is arranged to face the sample on the stage, and emits an electron beam as a secondary beam, an electron detection device which is arranged to face the sample, causes to project, as a primary beam, at least one of a secondary electron, reflected electron, and back-scattering electron generated by the sample upon irradiation of the electron beam, and generates image information of the sample, a stage driving device which is adjacent to the stage to drive the stage, and a deflector arranged between the sample and the electron detection device to deflect the secondary beam, the electron detection device having a converter arranged on a detection surface to convert the secondary beam into light, an array image sensing unit which is adjacent to the converter, has pixels of a plurality of lines each including a plurality of pixels on the detection surface, sequentially transfers charges of pixels of each line generated upon reception of light of an optical image obtained via the converter to corresponding pixels of an adjacent line at a predetermined timing, adds, every transfer, charges generated upon reception of light after the transfer at the pixels which received the charges, and sequentially outputs charges added up to a line corresponding to an end, and a control unit connected to the array image sensing unit to output a transfer signal for sequentially transferring charges of pixels of each line to an adjacent line, and the control unit having a stage scanning mode in which the array image sensing unit is controlled in accordance with a variation in projection position of the secondary beam projected on the electron detection device that is generated by movement of the stage device, and a deflector operation mode in which the array image sensing unit is controlled in accordance with a variation in projection position of the secondary beam projected on the detection device by the deflector.

6 Claims, 11 Drawing Sheets

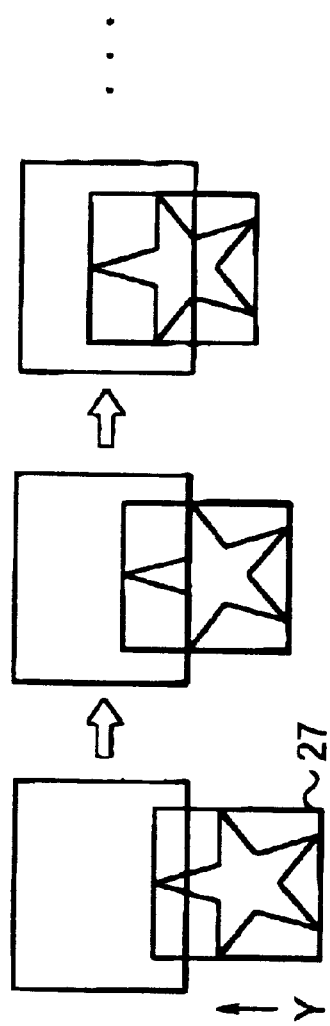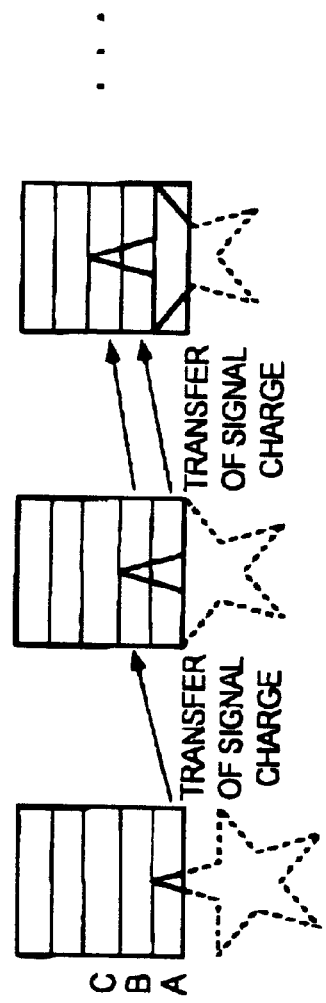

OBJECT OBSERVATION APPARATUS AND OBJECT OBSERVATION

RELATED APPLICATIONS

This is a Continuation-in-part application of International Patent Application Serial No. PCT/JP98/03667 filed on Aug. 19, 1998, now pending.

BACKGROUND OF THE INVENTION

1. Field of the Invention

The present invention relates to an object observation apparatus and, more particularly, to an apparatus and method of observing the integrated circuit pattern of a semiconductor wafer or the like using, e.g., an electron beam.

2. Related Background Art

With higher integration degrees of recent LSIs, the defect detection sensitivity required for samples such as a wafer and mask is increasing. For example, to detect defective portions on a wafer pattern 0.25 $\mu$m in DRAM pattern size, a detection sensitivity of 0.1 $\mu$m is required. In addition, demands have arisen for inspection apparatuses which satisfy both an increase in detection sensitivity and an increase in detection speed. To meet these requirements, surface inspection apparatuses using an electron beam have been developed.

A known example of an apparatus for scanning an electron beam on an object and observing secondary electrons from the object is a scanning electron microscope (SEM). A known example of an inspection apparatus for inspecting defects using an electrooptic system as a primary optical system is one disclosed in Japanese Patent Laid-Open No. 7-181297 (corresponding to U.S. Pat. No. 5,498,874). As disclosed in Japanese Patent Laid-Open No. 7-249393 (corresponding to U.S. Pat. No. 5,576,833), a pattern inspection apparatus is known which forms the sectional shape of a beam into a rectangular or elliptic shape through a rectangular cathode and quadrupole lens.

SUMMARY OF THE INVENTION

However, the conventional apparatuses are difficult to realize high-precision observation of an object using an electron beam.

It is, therefore, an object of the present invention to provide an observation apparatus and observation method capable of observing a clear image of an object to be observed at a high precision.

It is another object of the present invention to provide an object observation apparatus characterized by comprising a drivable stage on which a sample is placed, an irradiation optical system which is arranged to face the sample on the stage, and emits an electron beam as a primary beam, an electron detection device which is arranged to face the sample, has a detection surface on which at least one of a secondary electron, reflected electron, and back-scattering electron generated by the sample upon irradiation of the electron beam is projected as a secondary beam, and generates image information of the sample, a stage driving device which is adjacent to the stage to drive the stage, and a deflector arranged between the sample and the electron detection means to deflect the secondary beam, the electron detection device having a converter arranged on the detection surface to convert the secondary beam into light, an array image sensing unit which is adjacent to the converter, has pixels of a plurality of lines each including a plurality of pixels, sequentially transfers charges of pixels of each line generated upon reception of light of an optical image obtained via the converter to corresponding pixels of an adjacent line at a predetermined timing, adds, every transfer, charges generated upon reception of light after the transfer at the pixels which received the charges, and sequentially outputs charges added up to a line corresponding to an end, and a control unit connected to the array image sensing unit to output a transfer signal for sequentially transferring charges of pixels of each line to an adjacent line, and the control unit having a stage scanning mode in which the array image sensing unit is controlled in accordance with a variation in projection position of the secondary beam projected on the electron detection device that is generated by movement of the stage device, and a deflector operation mode in which the array image sensing unit is controlled in accordance with a variation in projection position of the secondary beam projected on the detection device that is generated by operation of the deflector.

It is still another object of the present invention to provide an object observation apparatus comprising an irradiation optical system which is arranged to face a sample, and irradiates the sample surface with an electron beam, an electron detection device which is arranged to face the sample, and detects as a secondary beam at least one of a secondary electron, reflected electron, and back-scattering electron generated by the sample upon irradiation of the electron beam, a deflector arranged between the irradiation optical system and electron detection device and the sample, irradiates the sample surface with the electron beam from the irradiation optical system, and guides a primary beam generated by the sample to the electron detection device, an objective electrooptic system arranged between the deflector and the sample, and a limiting member arranged at a focus position of the objective electrooptic system to limit the secondary beam amount, wherein the objective electrooptic system and limiting member constitute a telecentric electrooptic system.

It is still another object of the present invention to provide an object observation method of observing an object using an electron beam, characterized by comprising the irradiation step of irradiating the object on a stage with the electron beam, the conversion step of projecting a secondary beam from the irradiated object onto a fluorescent portion, and converting the secondary beam into light at the fluorescent portion, and the image sensing step of detecting image information of the light, converted at the fluorescent portion, with pixels of a plurality of lines each including a plurality of pixels, sequentially transferring charges generated in pixels of each line to corresponding pixels of an adjacent line at a predetermined timing, adding, every transfer, charges generated upon reception of light after the transfer at the pixels which received the charges, and sequentially outputting charges added up to a line corresponding to an end, the image sensing step having a stage scanning mode in which a projection position of the secondary beam from the object moving with movement of the stage is varied, and a deflector operation mode in which the projection position of the secondary beam from the object is varied by operating a deflector.

It is still another object of the present invention to provide an object observation apparatus characterized by comprising a drivable stage on which a sample is placed, an irradiation optical system which is arranged to face the sample on the stage, and emits an electron beam, an electron detection device which is arranged to face the sample, has a detection surface on which at least one of a secondary electron, reflected electron, and back-scattering electron generated by the sample upon irradiation of the electron beam is projected as a secondary beam, and generates image information of the sample, an electrooptic system arranged between the sample and the electron detection device to form the secondary beam into an image on the detection surface of the electron detection device, and a position detection device which is adjacent to the stage to detect a position of the stage, the electron detection device having a converter arranged on the detection surface to convert the secondary beam into light, an array image sensing unit which is adjacent to the converter, has pixels of a plurality of lines each including a plurality of pixels, sequentially transfers charges of pixels of each line generated upon reception of light of an optical image obtained via the converter to corresponding pixels of an adjacent line at a predetermined timing, adds, every transfer, charges generated upon reception of light after the transfer at the pixels which received the charges, and sequentially outputs charges added up to a line corresponding to an end, and a control unit connected to the array image sensing unit to output a transfer signal for sequentially transferring charges of pixels of each line to an adjacent line, the control unit controlling the array image sensing unit using a detection signal from the position detection device.

BRIEF DESCRIPTION OF THE DRAWINGS

FIGS. 7A to 7F are views for explaining the operation principle of a TDI array;

DESCRIPTION OF THE PREFERRED EMBODIMENTS

Figure 1:
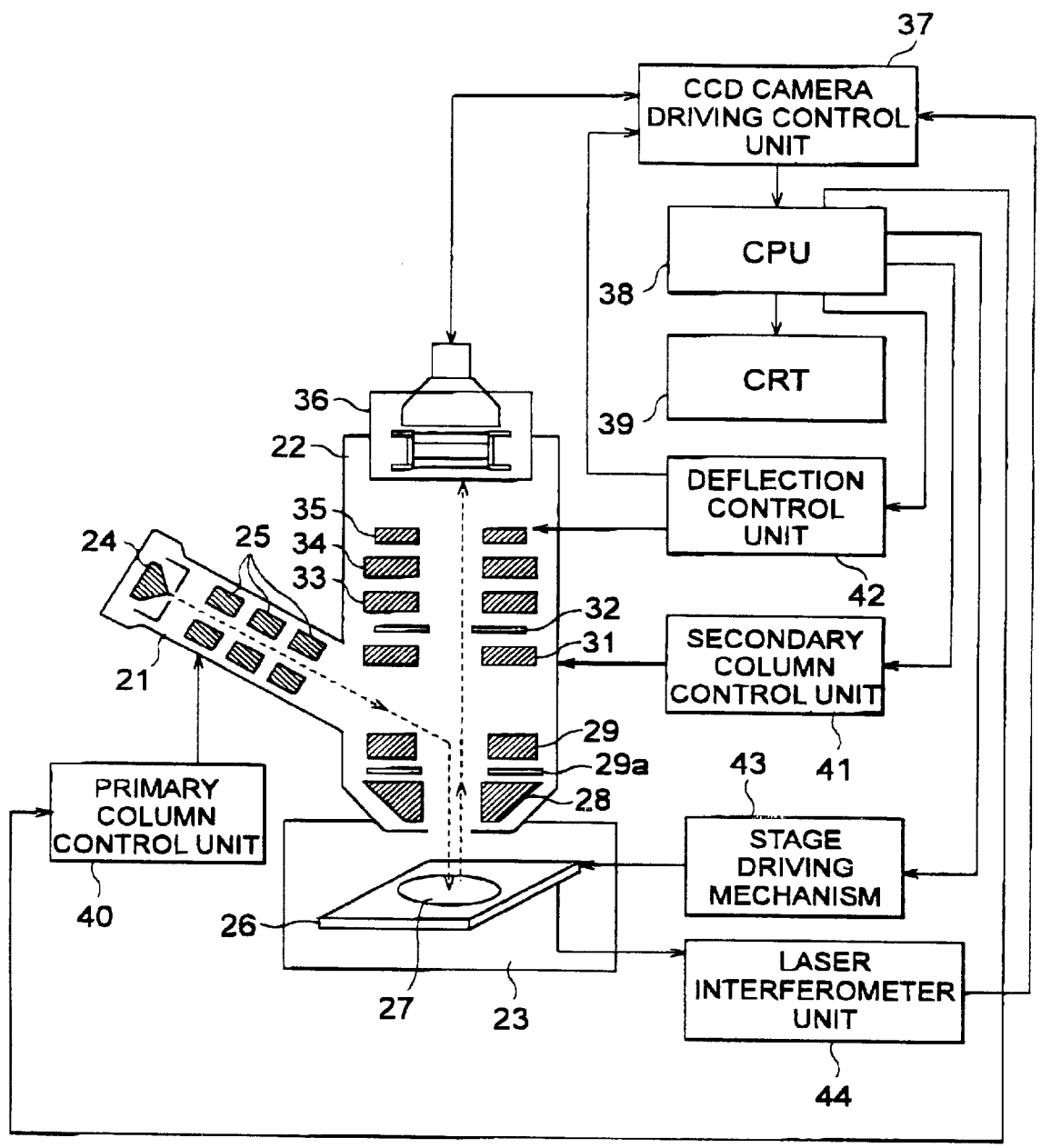
FIG. 1 is a view showing the whole arrangement of an object observation apparatus according to an embodiment of the present invention.

An embodiment of the present invention will be described with reference to the accompanying drawings. The same reference numerals denote the same parts throughout the drawings, and a repetitive description thereof will be omitted.

Figure 2:
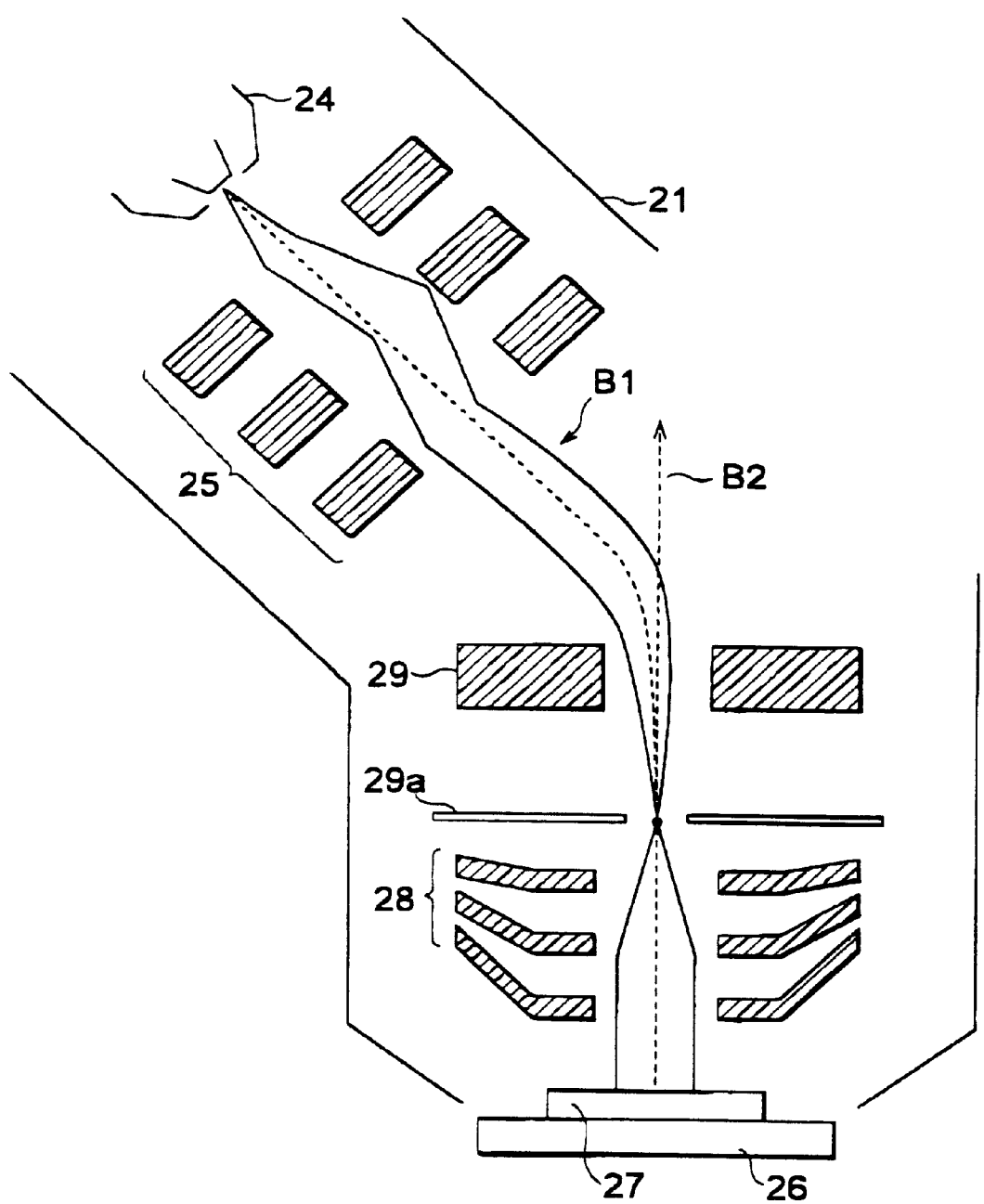
FIG. 2 is a view for explaining the structure of a primary column and the orbit of a primary beam in the object observation apparatus shown in FIG. 1.

FIG. 1 is a view showing the whole arrangement of the embodiment. FIG. 2 is a view showing the structure of a primary column and the orbit of a primary beam. FIG. 3 shows views of the structure of an electrostatic lens in the primary column. FIG. 4 is a view showing the orbit of a secondary beam in a secondary column.

As shown in FIG. 1, an observation apparatus comprises a primary column 21, secondary column 22, and chamber 23.

The primary column 21 is diagonally connected to the side surface of the secondary column 22, and the chamber 23 is located below the secondary column 22.

The primary column 21 incorporates an electron gun 24. A primary optical system 25 is located on the optical path of an electron beam (primary beam) emitted by the electron gun 24. A Wien filter 29 in the secondary column 22 is located diagonally to the optical axis ahead of the primary optical system 25.

The chamber 23 incorporates a stage 26 on which a sample 27 is placed.

In the secondary column 22, a cathode lens 28, the Wien filter 29, a numerical aperture 29a, a first lens 31, a field aperture 32, a second lens 33, a third lens 34, a deflector 35, and a detector 36 are arranged on the optical path of a secondary beam generated by the sample 27.

Note that the numerical aperture 29a corresponds to an aperture stop, and is made of a thin film of a metal (Mo or the like) having a circular hole. This aperture portion is positioned at the convergent position of the primary beam and a pupil position serving as the focus position of the cathode lens 28 to which a parallel beam from the sample is focused by the cathode lens 28. Thus, the cathode lens 28 and numerical aperture 29a constitute a telecentric electrooptic system.

A primary beam from the electron gun 24 is incident on the Wien filter 29 while being influenced by lens operation through the primary optical system 25. The electron gun chip is made of $LaB_6$ from which a large current can be extracted by a rectangular cathode. The primary optical system 25 uses a quadrupole or octupole electrostatic (electromagnetic) lens asymmetrical about the axis of rotation. This lens can cause convergence and divergence on each of the x- and y-axes, similar to a so-called cylindrical lens. This lens is formed from two or three lenses, and the conditions of each lens are optimized. This makes it possible to form a beam irradiation region on the sample surface into an arbitrary rectangular or elliptic shape without losing any irradiation electrons.

Figure 3A:
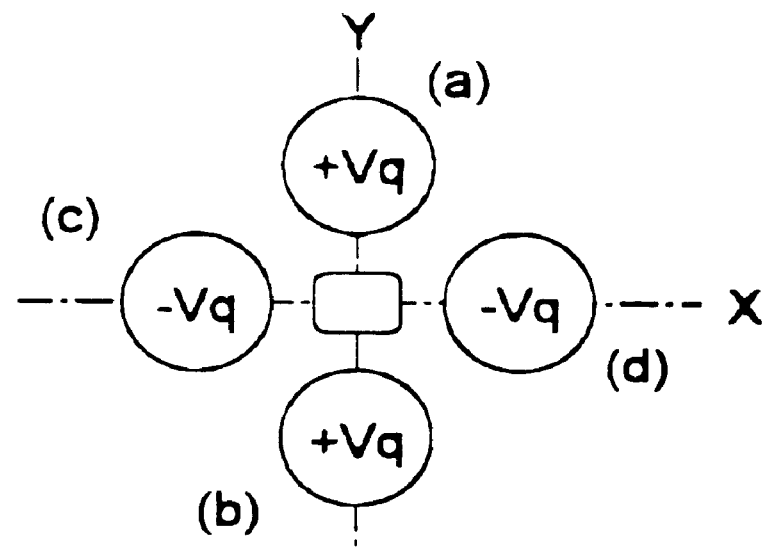
FIGS. 3A and 3B are views each for explaining the structure of an electrostatic lens in the primary column shown in FIG. 2.
Figure 3B:
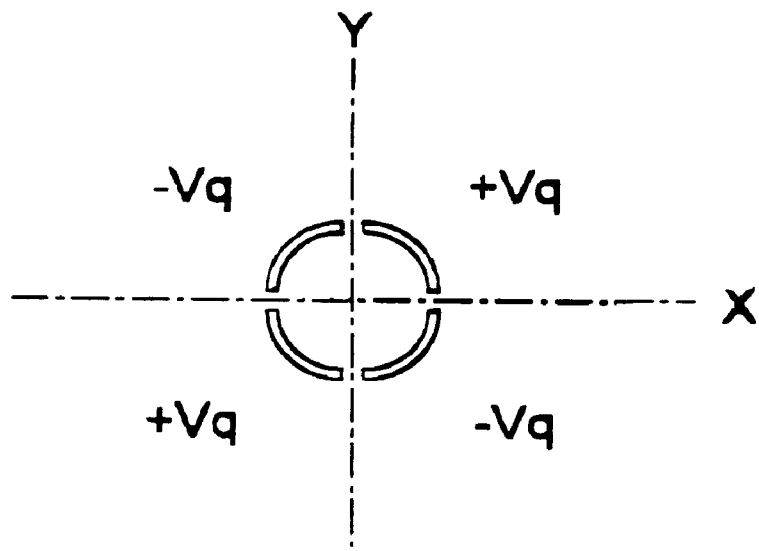
Figure 4:
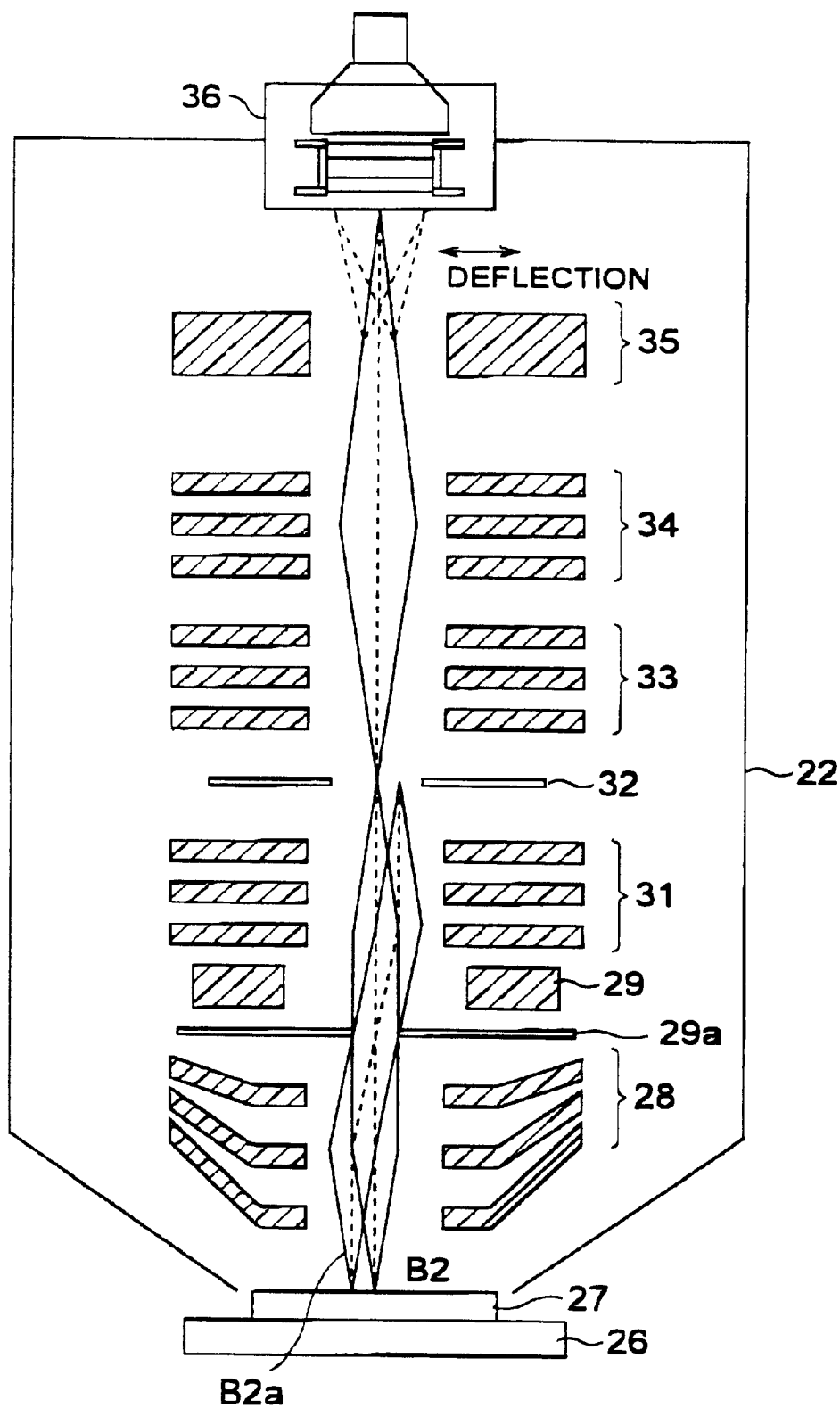
FIG. 4 is a view for explaining the structure of a secondary column and the orbit of a secondary beam in the object observation apparatus shown in FIG. 1.

More specifically, when an electrostatic lens is used, as shown in FIG. 3A, four columnar rods are used. Facing electrodes (a-b or c-d) are set at the same potential and given opposite voltage characteristics. Instead of the columnar quadrupole lens, lenses obtained by dividing a generally used circular plate may be used in an electrostatic deflector, as shown in FIG. 3B. In this case, the lens can be downsized.

As shown in FIG. 2, the orbit of a primary beam B1 having passed through the primary optical system 25 is deflected by the deflecting operation of the Wien filter 29. Assume that the magnetic field and electric field cross at a right angle, and E, B, and v represent the electric field, magnetic field, and charged-particle speed, respectively. In this case, the Wien filter 29 allows only charged particles that satisfy the Wien condition of $E=vB$ to travel straight, and deflects the remaining charged particles.

Figure 5A:
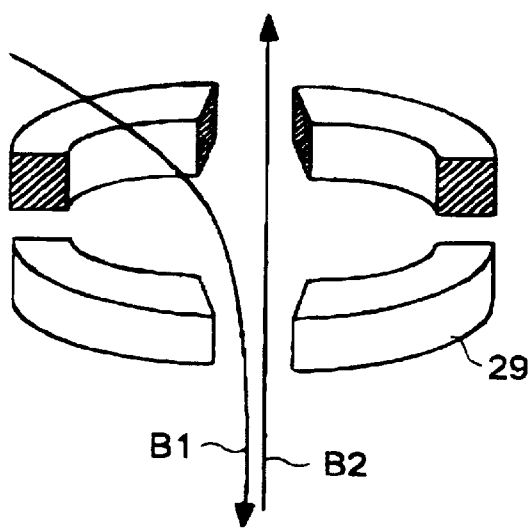
FIGS. 5A, 5B, and 5C are views for explaining the structure and operation principle of a Wien filter 29 used in the object observation apparatus shown in FIG. 1.
Figure 5B:
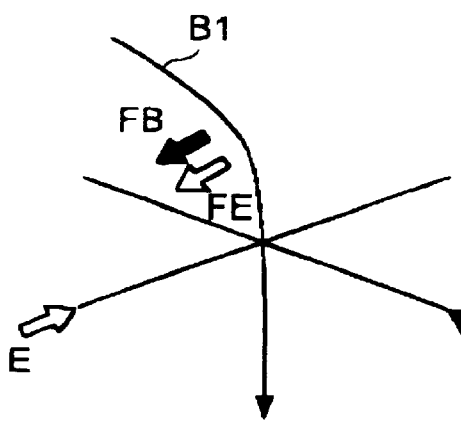
Figure 5C:
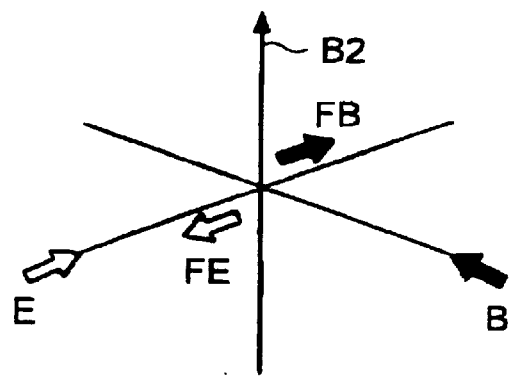

The function of the Wien filter will be explained. As shown in FIGS. 5A, 5B, and 5C, a force FB by the magnetic field and a force FE by the electric field are generated for the primary beam B1 to deflect its beam orbit. As for a secondary beam B2, the forces FB and FE act in opposite directions and cancel each other, and thus the secondary beam B2 travels straight.

The lens voltage of the primary optical system 25 is set in advance so as to form a primary beam into an image at the aperture portion of the numerical aperture 29a. This numerical aperture 29a prevents a redundant electron beam scattering in the apparatus from reaching the sample surface, and prevents charge-up and contamination of the sample 27.

The numerical aperture 29a and cathode lens 28 constitute a telecentric optical system. Hence, as shown in FIG. 2, a primary beam having passed through the cathode lens 28 becomes a parallel beam, which uniformly irradiates the sample 27. That is, so-called Köhler illumination in an optical microscope is realized.

The primary beam having passed through the cathode lens 28 vertically irradiates the sample 27 to give the secondary beam a clear electronic image without any shadow.

In this embodiment, the irradiation region of the primary beam irradiating the sample 27 is rectangular. Secondary electrons, reflected electrons, or back-scattering electrons are generated as a secondary beam from the entire beam irradiation region of the sample 27. This secondary beam has rectangular two-dimensional image information.

When the primary beam irradiates the sample, secondary electrons, reflected electrons, or back-scattering electrons are generated as a secondary beam from the beam irradiation surface of the sample.

The secondary beam passes through the lens while being influenced by the lens operation of the cathode lens 28. The cathode lens 28 is made up of three electrodes. The lowest electrode is designed to form a positive electric field with the potential on the sample 27 side, draw electrons (especially secondary electrons weak in directivity), and efficiently guide the electrons into the lens.

The lens operation is attained by applying a voltage between the first and second electrodes of the cathode lens 28 and setting the third electrode to a potential of 0. Alternatively, the cathode lens 28 may be made up of four electrodes.

The numerical aperture 29a is located at the focus Position of the cathode lens 28, i.e., the back-focus position from the sample 27.

As shown in FIG. 4, a bundle B2a of electron beams generated outside the center of the field of view (outside the axis) are also changed into parallel beams, which pass through the central position of the numerical aperture 29a without being eclipsed.

Note that the numerical aperture 29a functions to suppress the lens aberration of the first, second, and third lenses 31, 32, and 34 with respect to the secondary beam.

The secondary beam B2 having passed through the numerical aperture 29a travels straight and passes through the Wien filter 29 without being influenced by the deflecting operation of the Wien filter 29. By changing the electromagnetic field applied to the Wien filter 29, only electrons (e.g., secondary electrons, reflected electrons, or back-scattering electrons) having a specific energy pass through the deflector 35 and are formed into an image on the detection surf ace of the detector 36. At this time, electrons are free from any deflecting operation of the deflector 35.

If the secondary beam B2 is formed into an image by only the cathode lens 28, the lens operation becomes strong, and aberration readily occurs. To prevent this, the cathode lens 28 forms one image in cooperation with the first lens 31. The secondary beam is formed into an intermediate image at the field aperture 32 through the cathode lens 28 and first lens 31.

Generally in this case, the secondary optical system is often short in necessary enlargement magnification, and thus is constituted by the second and third lenses 33 and 34 as lenses for enlarging an intermediate image. The secondary lens is enlarged and formed into an image through the second and third lenses 33 and 34. In this case, a total of two images are formed. Note that the third and fourth lenses 33 and 34 may be combined to form one image (a total of two images).

The first to third lenses 31 to 34 are lenses symmetrical about the axis of rotation called unipotential or einzel lenses. Each lens has three electrodes. In general, the two outer electrodes are set to a potential of 0, and lens operation is attained and controlled by the voltage applied to the central electrode.

The field aperture 32 is set at the intermediate imaging point. This field aperture 32 limits the field of view to a necessary range, similar to the field stop of an optical microscope. For an electron beam, the field aperture 32 cuts off a redundant beam in cooperation with the second and third lenses 33 and 34 on the exit side to prevent chart-up and contamination of the detector 36. The enlargement magnification is set by changing the lens conditions of the second and third lenses 33 and 34, e.g., their focal lengths.

In this manner, in the first embodiment, the numerical aperture 29a and cathode lens 28 constitute a telecentric electrooptic system. As for the primary beam, the beam can uniformly illuminate a sample. That is, Köhler illumination can be easily realized.

As for the secondary beam, all principal rays from the sample 27 are incident on the cathode lens 28 vertically (parallel to the optical axis of the lens), and pass through the numerical aperture 29a. For this reason, marginal rays are not eclipsed, and the image brightness at the periphery of the sample does not decrease on the detection surface.

So-called aberration of magnification occurs in which the imaging position changes owing to variations in electron energy (in particular, secondary electrons cause a large aberration of magnification because of great variations in energy). However, this chromatic aberration of magnification can be suppressed by locating the numerical aperture 29a at the focus position of the cathode lens 28, i.e., making the aperture position coincide with the pupil position of the optical system.

Even if the distance between the sample 27 and cathode lens 28 varies, and focusing is executed, the enlargement magnification does not change because of the telecentric optical system. Focusing is done by changing the focal length of the cathode lens 28. Even if the focal length is changed, the arrangement of the telecentric electrooptic system does not change because the focal offset is very small.

The enlargement magnification is changed after a beam passes through the numerical aperture 29a. Even if set magnifications as the lens conditions of the second and third lenses 33 and 34 are changed, a uniform image can be obtained on the entire field of view on the detection side.

This embodiment can attain a uniform image. Further, the embodiment can keep the signal density of detection electrons constant to obtain an image having a constant brightness even if the enlargement magnification of the secondary optical system is increased by increasing the irradiation energy density of an electron beam.

As shown in FIG. 1, the input/output terminal of the detector 36 is connected to the input/output terminal of a CCD camera driving control unit 37. An output from the CCD camera driving control unit 37 is input to a CRT 39 via a CPU 38.

The CPU 38 outputs a control signal to a primary column control unit 40, secondary column control unit 41, deflection control unit 42, and stage driving mechanism 43.

The primary column control unit 40 controls the lens voltage of the primary optical system 25, and the secondary column control unit 41 controls the lens voltages of the cathode lens 28, first lens 31, second lens 33, and third lens 34. The deflection control unit 42 controls a voltage applied to the deflector 35, and the stage driving mechanism 43 controls driving of the stage 26 in the x and y directions.

The CCD camera driving control unit 37 receives a control signal from a laser interferometer unit 44 and a control signal from the deflection control unit 42.

The primary column 21, secondary column 22, and chamber 23 are connected to an evacuation system (not shown), and evacuated by the turbopump of the evacuation system to keep their insides vacuum.

Figure 6:
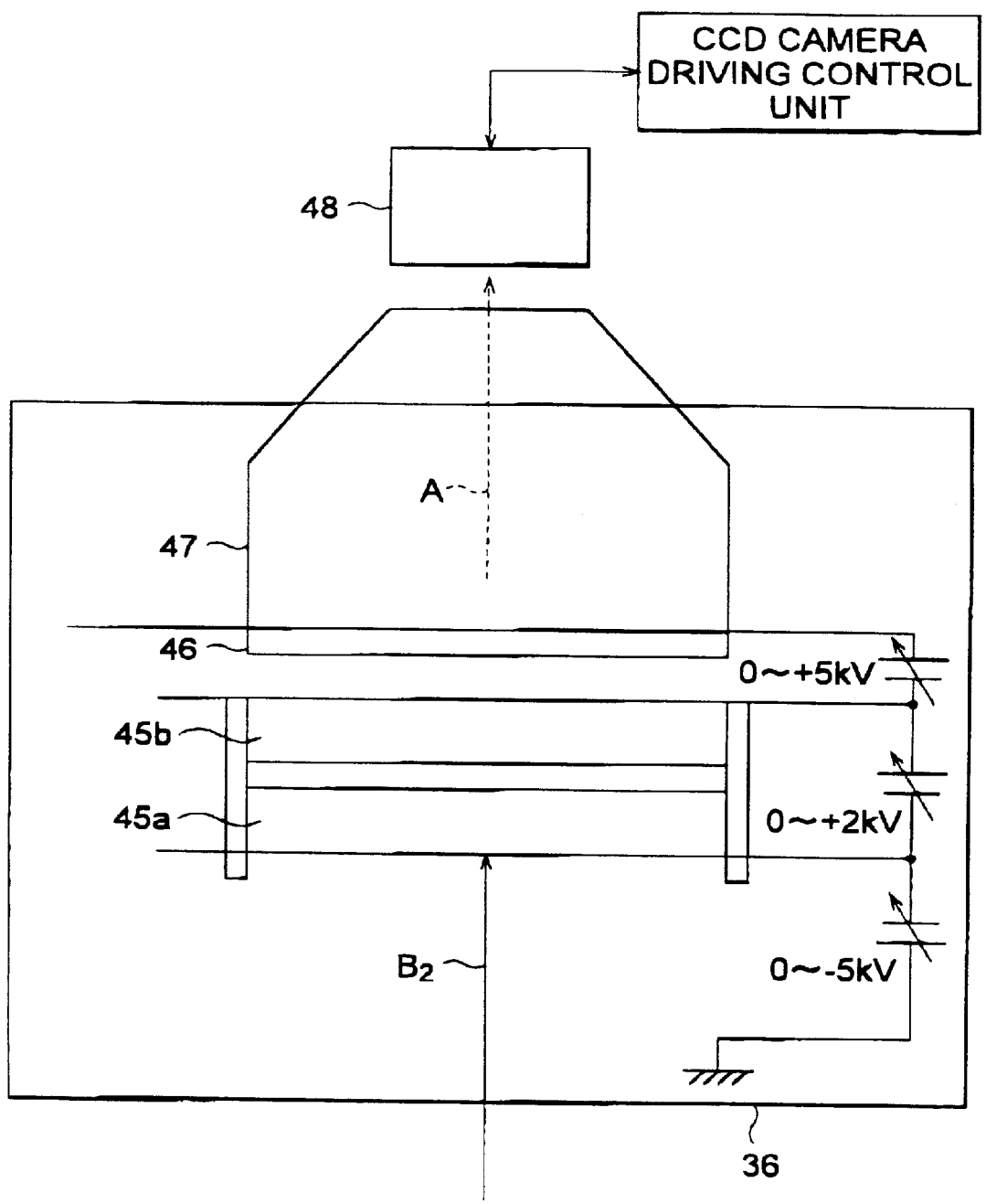
FIG. 6 is a view showing the structure of a detector 36 used in the object observation apparatus of the embodiment shown in FIG. 1.

FIG. 6 shows the structure of the detector 36. The detector 36 is constituted by a first MCP (Micro Channel Plate) 45a, second MCP 45b, FOP (Fiber Optic Plate) 47 having a fluorescent surface 46, and CCD camera 48 having a TDI array CCD sensor.

Image sensing operation of the TDI array CCD sensor used in the object observation apparatus will be explained with reference to FIGS. 7A to 7F.

As shown in FIG. 7A, an electron beam irradiates a predetermined portion of the sample 27. At this time, as shown in FIG. 7B, the TDI array CCD sensor accumulates signal charges in a horizontal scanning line A corresponding to the portion irradiated with the electron beam. The CPU 38 moves the stage 26 and sample 27 at a predetermined timing by one horizontal scanning line in the y direction, as shown in FIG. 7C. At the same time, the CCD camera driving control unit 37 transfers signal charges accumulated in the line A to a line B. Hence, as shown in FIG. 7D, the sum of signal charges accumulated in previous image sensing operation and signal charges obtained in current image sensing operation is accumulated in the line B.

As shown in FIG. 7E, the CRT 39 further moves the stage 26 and sample 27 by one horizontal scanning line. At the same time, as shown in FIG. 7F, the CCD camera driving control unit 37 transfers the signal charges of the line A to the line B and the signal charges of the line B to a line C. As a result, the sum of signal charges obtained in second previous, previous, and current image sensing operations is accumulated in the line C.

By repeating the above operation, signal charges at the same portion of the sample can be added and accumulated by the number of horizontal scanning lines. In other words, the TDI array CCD sensor can delay signal charges to repeat image sensing operation, thereby accumulating and increasing signal charges at the same portion of the sample. This can increase the current density of the sample and the S/N ratio of a detected image.

As shown in FIG. 4, the secondary beam B2 is incident on the first MCP 45a. While the current amount is amplified within the first MCP 45a, the secondary beam B2 passes through the second MCP 45b and collides against the fluorescent surface 46. At this time, the incident potential of the first MCP 45a is adjusted to set the acceleration voltage of the secondary beam to a value having the highest detection efficiency of the MCP.

For example, when the acceleration voltage of the secondary beam is +5 kv, the incident potential of the first MCP 45a is set to −4.5 kV to decelerate and set the electron energy to about 0.5 keV.

The current amplification factor of the secondary beam is defined by a voltage applied between the first and second MCPs 45a and 45b. For example, when a voltage of 1 kV is applied, the amplification factor is 1×104. In order to suppress spread of a secondary beam output from the second MCP 45b as much as possible, a voltage of about 4 kV is applied between the second MCP 45b and fluorescent surface 46.

On the fluorescent surface 46, electrons are converted into an optical image. The optical image passes through the FOP 47 and is sensed by the CCD camera 48. To make the image size on the fluorescent surface 46 match the image sensing size of the CCD camera 48, the FOP 47 reduces the optical image to about ⅓, and projects the reduced image.

The optical image is photoelectrically converted by the TDI array CCD sensor of the CCD camera 48, and signal charges are accumulated in the TDI array CCD sensor. The CCD camera driving control unit 37 serially reads out image information from the TDI array CCD sensor, and outputs the information to the CPU 38. The CPU 38 displays the detected image on the CRT 39.

Figure 8:
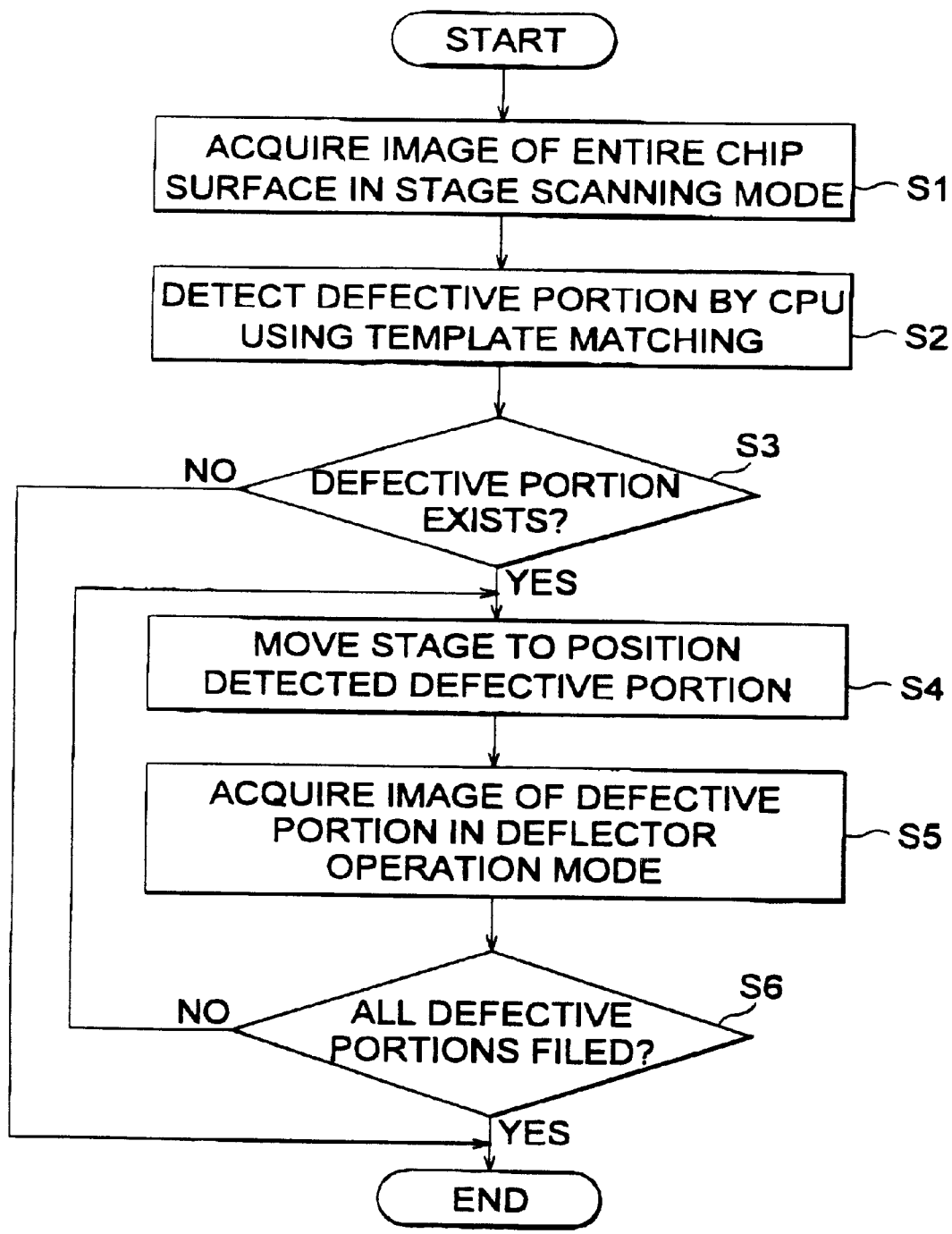
FIG. 8 is a flow chart for explaining defective portion detecting operation executed in the object observation apparatus of the embodiment shown in FIG. 1.

Next, a stage scanning mode and deflector operation mode as operations according to this embodiment will be described with reference to the accompanying drawings. FIG. 8 is a flow chart for explaining defective portion detecting operation.

Operation Mode

Stage Scanning Mode

Figure 9A:
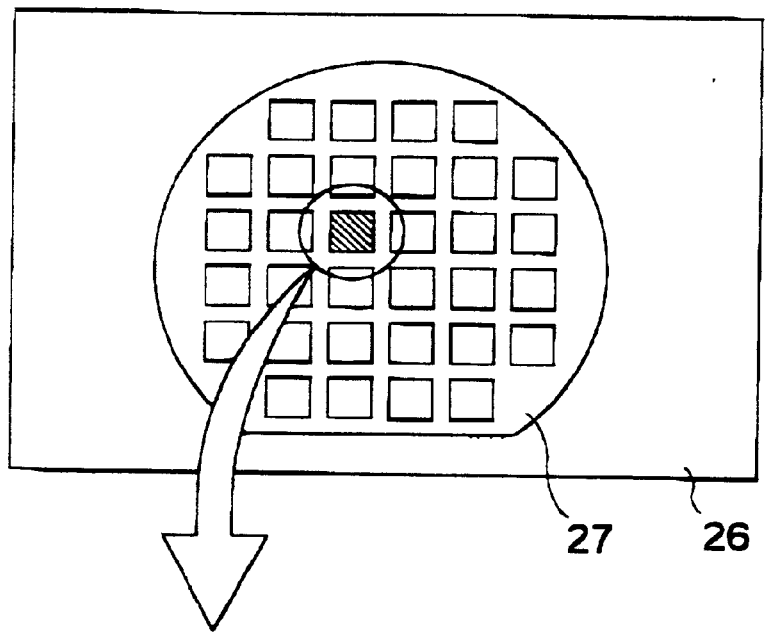
FIGS. 9A and 9B are views for explaining a stage scanning mode executed in the object observation apparatus of the embodiment shown in FIG. 1.
Figure 9B:
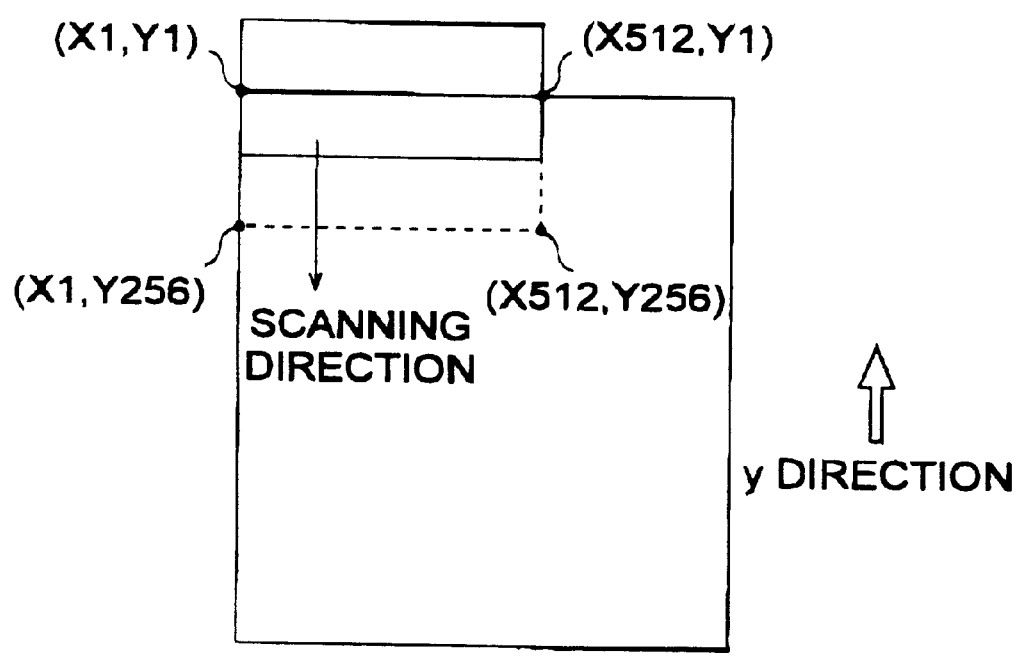

When the sample is a semiconductor wafer, as shown in FIGS. 9A and 9B, raster scanning is executed to detect an image on the entire chip. FIG. 9B is an enlarged view of one chip in FIG. 9A. The primary beam irradiates a fixed position and scans the sample surface by driving the stage 26.

The sample on the stage 26 moves at a constant speed in the y direction by the CPU 38 and stage driving mechanism 43.

In this case, a region from (X1, Y1) to (X512, Y256) is set as a region to be inspected. The TDI array CCD sensor has, e.g., 512×256 pixels, and the region to be inspected is projected to match the TDI array CCD sensor.

An image from (X1, Y1) to (X512, Y1) as the region to be inspected is sensed by the TDI array CCD sensor. Signal charges are accumulated in ROW 1 of the TDI array CCD sensor shown in FIG. 10. The stage 26 moves in the y direction in accordance with an instruction from the CPU 38, and then the beam irradiation region moves in the scanning direction by one horizontal scanning line of the TDI array CCD sensor. At the same time, the laser interferometer unit 44 outputs a vertical clock signal to the CCD camera driving control unit 37.

Upon reception of the vertical clock signal, the CCD camera driving control unit 37 outputs a transfer pulse to transfer signal charges accumulated in ROW 1 to ROW 2. In ROW 2, signal charges obtained by sensing an image from (X1, Y1) to (X512, Y1) have been accumulated. These signal charges are added to signal charges transferred from ROW 1, and the sum is accumulated. Then, an image from (X1, Y2) to (X512, Y2) is sensed, and its signal charges are accumulated in ROW 1.

In this way, the primary beam scans the region to be inspected by sequentially driving the stage 26 in the y direction. Accumulated charges are sequentially transferred to an adjacent row in accordance with driving of the stage.

When an image from (X1, Y256) to (x512, Y256) as the region to be inspected is sensed and accumulated in ROW 1 of the TDI array CCD sensor, an image from (X1, Y1) to (X512, Y1) is cumulated by the number of horizontal scanning lines and accumulated in ROW 256 of the TDI array CCD sensor.

If a transfer pulse is input to the TDI array CCD sensor in this state, signal charges accumulated in ROW 256 are transferred to a CCD shift register via a transfer gate (not shown), and output to the CPU 38 via the CCD camera driving control unit 37.

By sequentially driving the stage 26, the primary beam scans the sample, and the sample image is extracted from the TDI array CCD sensor in units of horizontal scanning lines.

This operation is executed for the entire chip surface to acquire an image of the entire chip surface (step S1 in FIG. 8).

After the image of the entire chip surface is acquired, the CPU 38 specifies a defective portion by template matching with a template image prepared in advance based on design data. More specifically, the CPU 38 reduces noise by smoothing processing using an edge-preserved smoothing filter, and then calculates the correlation coefficient between the template image and detected image, thereby specifying an unmatched portion, i.e., defective portion (step S2 in FIG. 8). The CPU 38 stores the address of the defective portion in an internal memory.

Deflector Operation Mode

The deflector operation mode in which a defective portion is enlarged and displayed when the defective portion is detected (step S3 in FIG. 8) will be explained.

The CPU 38 drives the stage 26 via the stage driving mechanism 43 to position the defective portion (step S4 in FIG. 8). The CPU 38 changes the focal lengths of the second and third lenses 33 and 34 to enlarge and display the defective portion.

Figure 10:
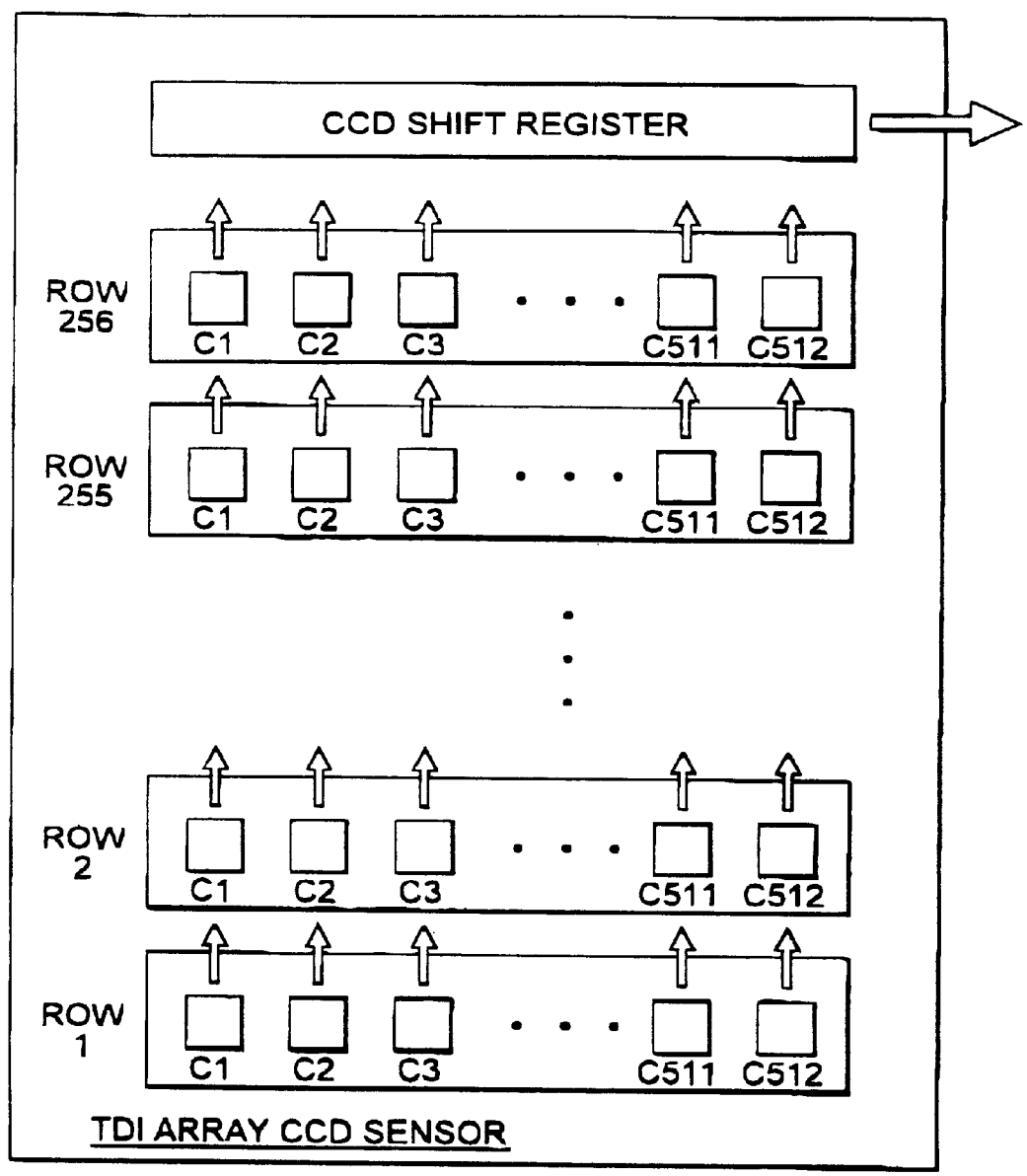
FIG. 10 is a block diagram showing the arrangement of a TDI array sensor used in the embodiment shown in FIG. 1.
Figure 11A:
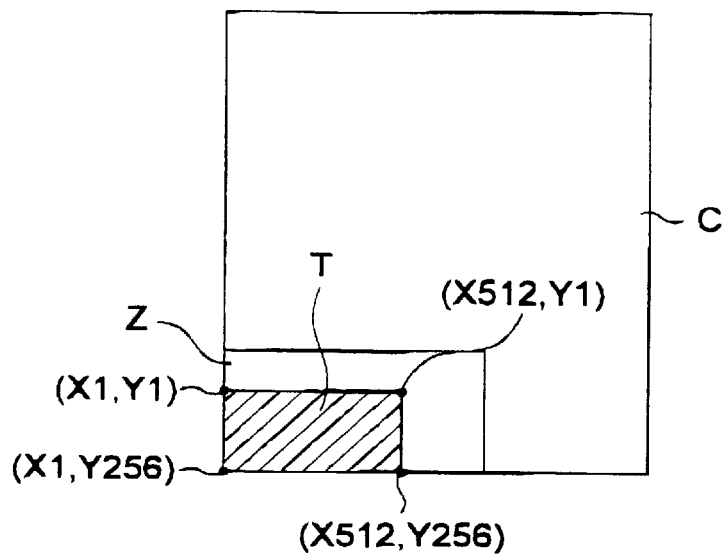
FIGS. 11A and 11B are views for explaining a deflector operation mode executed in the object observation apparatus of the embodiment shown in FIG. 1.

As shown in FIG. 11A, an image from (X1, Y1) to (X512, Y1) in a region T to be inspected at the defective portion in a beam irradiation region Z on the chip C is sensed and accumulated in ROW 1 of the TDI array CCD sensor in FIG. 10.

Figure 11B:
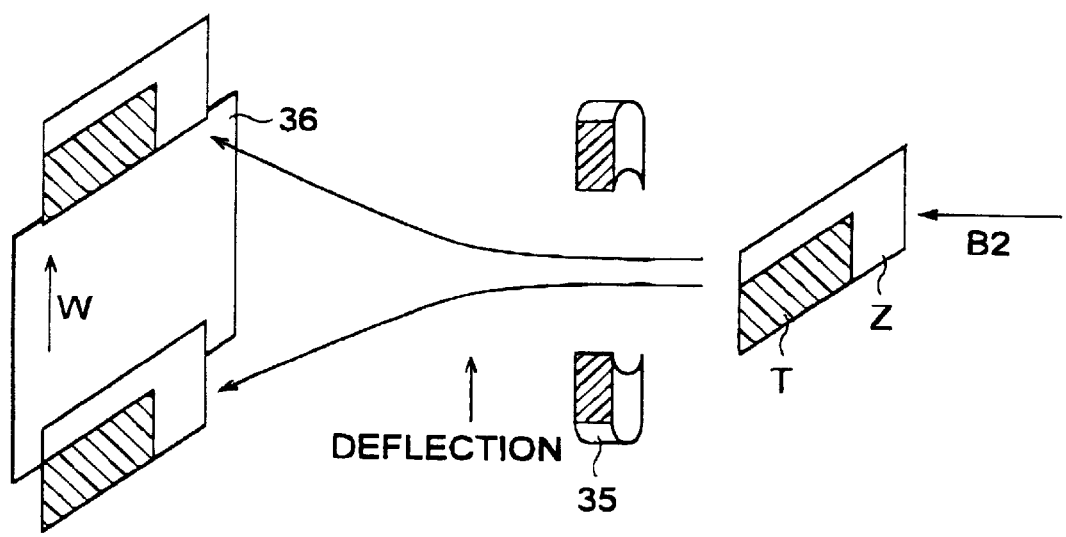

The CPU 38 calculates a voltage value to be applied to the deflector 35 on the basis of a set enlargement magnification, and outputs a control signal to the deflection control unit 42. The deflection control unit 42 controls the voltage applied to the deflector 35 in accordance with the control signal from the CPU 38. As shown in FIG. 11B, the projection position of a secondary beam projected on the detection surface of the detector 36 is deflected and moved by one horizontal scanning line in an arrow direction W in FIG. 11B.

At the same time, the deflection control unit 42 outputs a vertical clock signal to the CCD camera driving control unit 37. The CCD camera driving control unit 37 outputs a transfer pulse to transfer signal charges accumulated in ROW 1 to ROW 2.

In ROW 2, signal charges obtained by sensing an image from (X1, Y1) to (X512, Y1) have been accumulated. These signal charges are added to signal charges transferred from ROW 1, and the sum is accumulated. Then, an image from (X1, Y2) to (X512, Y2) is sensed, and its signal charges are accumulated in ROW 1.

In this fashion, the region to be inspected is scanned by sequentially moving the projection position of the secondary beam by the deflector 35. At this time, accumulated signal charges are sequentially transferred to an adjacent row in accordance with the projection position of the secondary beam. When an image from (X1, Y256) to (X512, Y256) as the region to be inspected is sensed and accumulated in ROW 1 of the TDI array CCD sensor, an image from (X1, Y1) to (X512, Y1) is added by the number of horizontal scanning lines and accumulated in ROW 256 of the TDI array CCD sensor.

If a transfer pulse is input in this state, signal charges accumulated in ROW 256 are transferred to the CCD shift register via the transfer gate (not shown), and output to the CPU 38 via the CCD camera driving control unit 37.

By sequentially moving the projection position of the secondary beam by the deflector 35, the sample image is extracted from the TDI array CCD sensor in units of horizontal scanning lines. The CPU 38 can acquire an image at the defective portion (step S5 in FIG. 8).

This operation is executed for all the defective portions, and repeated until the images of the defective portions are sequentially acquired and stored as an image file in a recording medium (step S6 in FIG. 8).

For the entire chip surface, the object observation apparatus of the embodiment drives the stage 26 to execute beam scanning, and senses an image using the TDI array CCD sensor to detect a defective portion. For the defective portion, the apparatus moves the projection position of the secondary beam by the deflector 35 to scan the sample.

The object observation apparatus uses the stage scanning mode for detection of an image on the entire sample surface, and uses the deflector operation mode for the local region of the sample. Accordingly, the apparatus can detect the defective pattern of the sample at a high speed and high precision.

Especially in the local region, no image is sensed by driving the stage 26, so the stage 26 need not be controlled at a high precision. In addition, a decrease in S/N ratio of a detected image owing to hunting of the stage 26 poses a problem. However, the decrease in image quality can also be avoided.

As a sample scanning method, this embodiment executes raster scanning, but the present invention is not limited to this.

In the deflector operation mode, the beam irradiation region may be changed in accordance with the size of a defective portion. The shape of the beam irradiation region is not limited to a rectangular one.

The matching method in pattern matching is not limited to the method described in the embodiment, and may be another matching method such as SSDA (Sequential Similarity Detection Algorithm) or the residual sum of squares.

In the object observation apparatus of the embodiment, a defect detection device 9 detects a defective portion from image information of a sample by template matching or the like.

At this time, it is also possible to search for defective portions of the entire sample in the stage scanning mode and then finely observe each defective portion in the deflector operation mode.

This embodiment adopts the Wien filter 29 for deflecting the orbit of the primary beam and allowing the secondary beam to travel straight, but the present invention is not limited to this. The primary beam may travel straight, and secondary electrons or the like emitted by the sample may be detected. Alternatively, the orbit of the secondary beam may be deflected by the Wien filter and detected.

This embodiment forms a rectangular beam as a primary lens through the rectangular lens and quadrupole lens, but the present invention is not limited to this. A circular beam may be formed using a general electrostatic or electromagnetic lens symmetrical about the axis of rotation, and may be formed into a rectangular or elliptic beam. Instead, the circular beam may be extracted as a rectangular beam through a slit. In this case, the primary optical system can be realized with a simple arrangement. Since the primary optical system need not be made up of three lenses, this system can be electrically, mechanically downsized at a low cost.

As has been described above, the object observation apparatus according to the embodiment of the present invention has the stage scanning mode in which an electron beam scans a sample by driving the stage, and the deflector operation mode in which an image is sensed by moving the projection position of the secondary beam using the deflection means. For a large region to be inspected, the apparatus can use the stage scanning mode to detect an image at a high speed. For a small region, the apparatus can use the deflector operation mode to detect an image at a high sensitivity and high image quality. Especially in detecting an image of the local region, the stage must be stably controlled at a high precision. However, using the deflector operation mode eliminates complicated high-precision control of the stage. The apparatus can cope with detection of a very small region.

In this object observation apparatus, the stage scanning mode is suitable for detection of defects and confirmation of an image on the entire sample. The deflector operation mode is suitable for detection of defects in the local region of the sample. By using a combination of the two modes, defective portions of an image can be detected at a high speed and high precision. In this manner, the pattern inspection apparatus to which the present invention is applied can avoid a decrease in S/N ratio caused by vibrations of the stage without controlling driving of the stage at a high precision. Consequently, the inspection reliability can increase.

In this embodiment, the objective electrooptic system and beam limiting means constitute a telecentric electrooptic system. Hence, all the principal rays from a sample are vertically incident on the objective electrooptic system and pass the beam limiting means. Marginal rays are not eclipsed, and the image brightness at the periphery of the sample does not decrease. That is, a uniform, clear image can be acquired both at the periphery and center of the sample.

Even if the distance between the sample and objective electrooptic system varies, and focusing is executed, the enlargement magnification does not change because of the telecentric electrooptic system.

Since an electron beam is focused at the focus position of the objective electrooptic system, the electron beam uniformly irradiates the sample. That is, Köhler illumination can be easily realized. Even if an electron gun chip for emitting an electron beam suffers luminance irregularity, the intensity irregularity of the beam is unified by the objective electrooptic system, and the beam irradiates the sample. Thus, noise by intensity irregularity can be reduced.

Moreover, the sectional shape of the electron beam can be formed into a rectangular or elliptic shape. The beam irradiation region on the sample surface, therefore, has a predetermined rectangular or elliptic area. At this time, complicated lens control is required to uniformly irradiate the entire irradiation area with a beam. However, this embodiment can unify the electron beam to irradiate the entire area.

Since the observation apparatus to which the present invention is applied can increase the S/N ratio of an observation image, a high-reliability observation apparatus can be realized.

What is claimed is:

1. An object observation apparatus comprising:
   a drivable stage on which a sample is placed;
   an irradiation optical system which is arranged to face the sample on said stage, and emits an electron beam as a primary beam;
   an electron detector which is arranged to face the sample, has a detection surface on which at least one of a secondary electron, a reflected electron, and a back-scattering electron generated by the sample upon irradiation of the electron beam is projected as a secondary beam, and generates image information of the sample;
   a stage driver which is adjacent to said stage to drive said stage; and
   a deflector arranged between the sample and said electron detector to deflect the secondary beam,
   said electron detector having:
      a converter arranged on the detection surface to convert the secondary beam into light;
      an array image sensor which is adjacent to said converter, has pixels of a plurality of lines each including a plurality of pixels, sequentially transfers charges of pixels of each line generated upon reception of light of an optical image obtained via said converter to corresponding pixels of an adjacent line at a predetermined timing, adds, every transfer, charges generated upon reception of light after the transfer at the pixels which received the charges, and sequentially outputs charges added up to a line corresponding to an end; and
      a controller connected to said array image sensor to output a transfer signal for sequentially transferring charges of pixels of each line to an adjacent line, and
   said controller having:
      a stage scanning mode in which said array image sensor is controlled in accordance with a variation in projection position of the secondary beam projected on said electron detector that is generated by movement of said stage device; and
      a deflector operation mode in which said array image sensor is controlled in accordance with a variation in projection position of the secondary beam projected on said detector that is generated by operation of said deflector.

2. An object observation apparatus according to claim 1, further comprising a defect detector that detects a defective portion from the image information of the sample generated by said electron detector.

3. An object observation apparatus according to claim 1, wherein the electron beam has a rectangular or elliptic sectional shape.

4. An object observation method of observing an object using an electron beam, comprising:
   an irradiation step of irradiating the object on a stage with the electron beam;

a conversion step of projecting a secondary beam from the irradiated object onto a fluorescent portion, and converting the secondary beam into light at the fluorescent portion; and an image sensing step of detecting image information of the light, converted at the fluorescent portion, with pixels of a plurality of lines each including a plurality of pixels, sequentially transferring charges generated in pixels of each line to corresponding pixels of an adjacent line at a predetermined timing, adding, every transfer, charges generated upon reception of light after the transfer at the pixels which received the charges, and sequentially outputting charges added up to a line corresponding to an end, the image sensing step having:
- a stage scanning mode in which a projection position of the secondary beam from the object moving with movement of the stage is varied; and
- a deflector operation mode in which the projection position of the secondary beam from the object is varied by operating a deflector.

5. An object observation apparatus comprising:

a drivable stage on which a sample is placed;

an irradiation optical system which is arranged to face the sample on said stage, and emits an electron beam;

an electron detector which is arranged to face the sample, has a detection surface on which at least one of a secondary electron, a reflected electron, and a backscattering electron generated by the sample upon irradiation of the electron beam is projected as a secondary beam, and generates image information of the sample;

an electrooptic system arranged between the sample and said electron detector to form the secondary beam into an image on the detection surface of said electron detector; and a position detector which is adjacent to said stage to detect a position of said stage, said electron detector having:
- a converter arranged on the detection surface to convert the secondary beam into light;
- an array image sensor which is adjacent to said converter, has pixels of a plurality of lines each including a plurality of pixels, sequentially transfers charges of pixels of each line generated upon reception of light of an optical image obtained via said converter to corresponding pixels of an adjacent line at a predetermined timing, adds, every transfer, charges generated upon reception of light after the transfer at the pixels which received the charges, and sequentially outputs charges added up to a line corresponding to an end; and
- a controller connected to said array image sensor to output a transfer signal for sequentially transferring charges of pixels of each line to an adjacent line, said controller controlling said array image sensor using a detection signal from said position detector.

6. An object observation apparatus according to claim 5, further comprising:

a deflector arranged between the sample and said electron detector to deflect the secondary beam; and a deflector driver connected to said deflector to drive said deflector, and said controller controls said array image sensor by selectively using the detection signal and a control signal from said deflector driver.

* * * * *